United States Patent [19]

Ellett

[11] 4,280,167
[45] Jul. 21, 1981

[54] OPERATING ROOM SURGICAL LAMP
[76] Inventor: Edwin W. Ellett, 1000 Holik Dr., College Station, Tex. 77840
[21] Appl. No.: 75,092
[22] Filed: Sep. 13, 1979
[51] Int. Cl.³ .............................................. A61G 13/00
[52] U.S. Cl. ................................. 362/33; 362/216; 362/147; 362/304; 362/404
[58] Field of Search ................. 362/33, 216, 147, 304, 362/404

[56] References Cited
U.S. PATENT DOCUMENTS
2,896,066  7/1959  Quetin .................................... 362/33

Primary Examiner—Stephen J. Lechert, Jr.
Attorney, Agent, or Firm—Pravel, Gambrell, Hewitt, Kirk, Kimball & Dodge

[57] ABSTRACT

An improved operating room surgical lamp having a concave reflector housing, an inverted conical reflector disposed therein and one or more circular fluorescent lamps disposed within the concave reflector and about the inverted conical reflector. The surgical lamp of the present invention provides an evenly illuminated light field having a centrally illuminated portion of even greater illumination.

11 Claims, 8 Drawing Figures

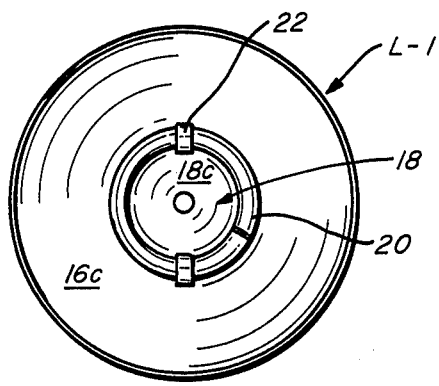
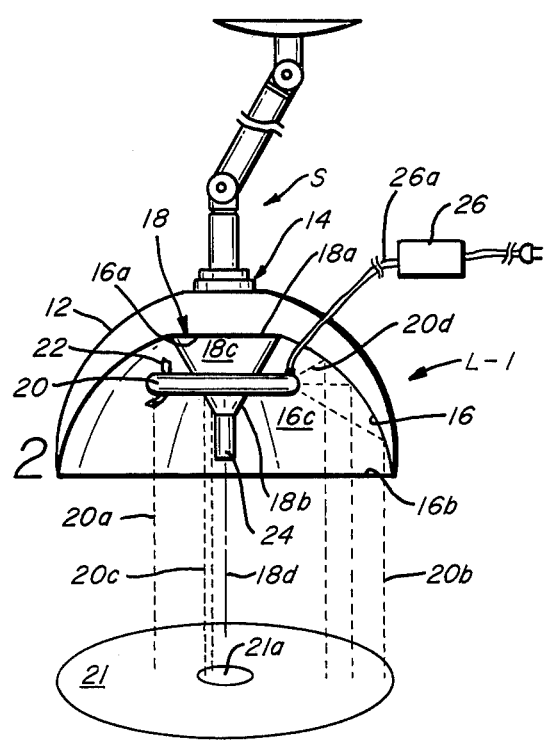
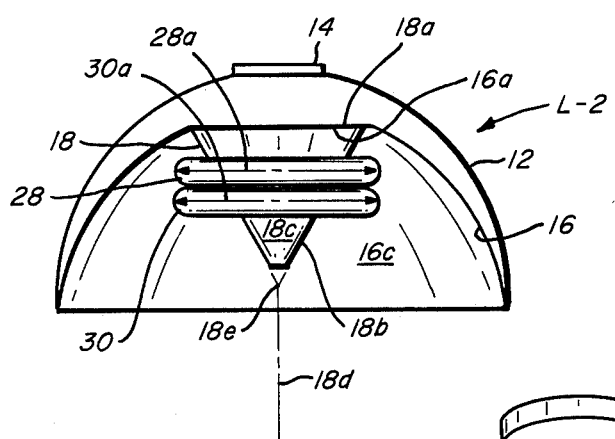
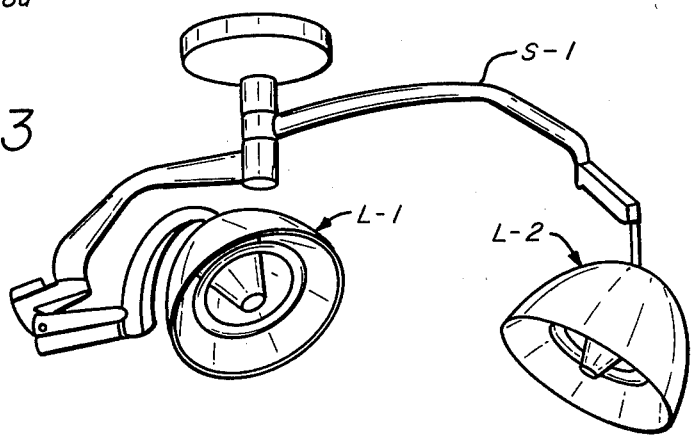
FIG. 1
FIG. 2
FIG. 2A
FIG. 3
FIG. 4

OPERATING ROOM SURGICAL LAMP

TECHNICAL FIELD OF THE INVENTION

The technical field of this invention is operating room surgical lamps.

Prior Art

Currently, operating room surgical lights consist of a housing having a reflector and one or more incandescent lamps obtained therein. The incandescent lamps themselves normally are of the quartz halogen type currently known in the art. Operating room surgical lights currently used tend to generate a great deal of heat which causes fatigue to the surgical staff and dries out the exposed tissue. The color temperature of the surgical room operating lamps is critical because of the requirement often times to identify pathological tissue and to photograph certain operations.

A dental operating lamp having a bowl-type or concave reflector and an incandescent light transmitting member disposed therein is taught by U.S. Pat. No. 2,280,402 of Greppin. In Greppin, an incandescent light is mounted centrally in the bowl-type reflector in a light transmitting cylinder member which may have another partial cylinder of opaque material mounted thereover. A lighting fixture having five frusto-conical reflectors nested in a cylindrical light transmitting enclosure positioned about the vertical axis of a light source is taught by U.S. Pat. No. 4,096,555 of Lasker. In U.S. Pat. No. 3,609,335 of Kelly, a high intensity surgical light is positioned in a frusto-conical reflector in a cylindrical housing over which is telescopically disposed an adjusting cylinder.

U.S. Pat. No. 3,786,244 of Hutter discloses a surgical lamp directing rays of light radially outwardly for reflectance off of an outer reflective ring toward the desired area of illumination. Other patents disclosing a central light source reflecting off a dome-shaped reflective member or bowl include U.S. Pat. Nos. 4,081,667; 4,038,542; 3,891,842; 3,711,700; 3,588,488 and 1,927,181.

SUMMARY OF THE INVENTION

Briefly, the present invention provides a new, improved operating surgical lamp comprising a housing, having a concave or bowl-type reflector disposed therein, an inverted conical reflector mounted therewith and a circular, tubular light source, preferably a circular fluorescent lamp, disposed within the concave reflector and about the inverted conical reflector.

The improved operating room surgical lamp of the present invention utilizes a fluorescent-type light source which provides a light color temperature in the preferred range of about 4800 degrees kelvin, but yet generates very little heat, since a greater amount of heat normally fatigues the surgical staff and accelerates the drying of tissue exposed during surgery. The improved operating room surgical lamp of the present invention provides an evenly illuminated light field having a central portion with even a greater illumination. The light field provided by the present invention allows the immediate area of the surgery to be more brightly illuminated while providing an even light field for the surrounding area. It is understood that the improved operating room surgical lamp of the present invention may be "gang mounted" in order to provide even greater illumination. In addition to providing a desirable color temperature without generating a great deal of heat, the present invention consumes considerably less electrical power than conventional surgical lights. This summary is not intended to be inclusive of all features of this invention nor should this summary be considered more than representative of the actual invention of Applicant, which is set forth in the claims.

BRIEF DESCRIPTION OF THE DRAWINGS

FIG. 1 is a bottom view of the improved operating room surgical lamp as viewed from the open end of the concave reflector into the lamp area, such lamp embodiment having a single, circular light source;

FIG. 2 is an elevation view, partly in section of the embodiment in FIG. 1;

FIG. 2a is a perspective view of the light field projected by the embodiments of the present invention;

FIG. 3 is an elevation view of a second embodiment of the invention illustrating the lamp, partly in section, with a plurality of circular light sources;

FIG. 4 is a perspective view of two lamps of any of the embodiments of the present invention operably mounted with a ceiling support;

DESCRIPTION OF THE PREFERRED EMBODIMENT

Figure 5:
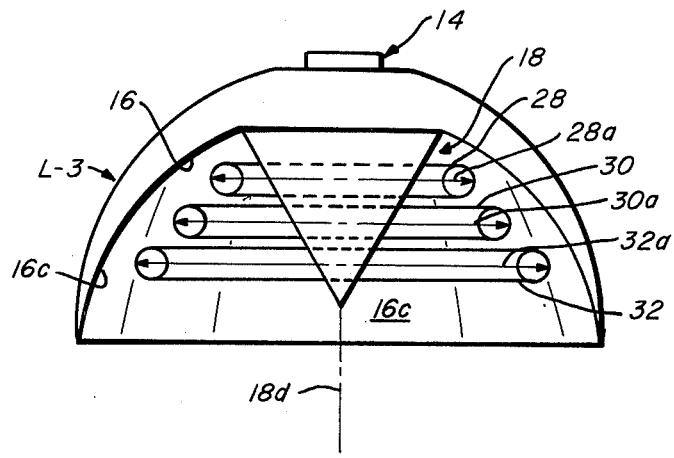
FIG. 5 is an elevation view of a third embodiment of the invention illustrating the lamp, partly in section, with a plurality of circular light sources.

The improved operating room surgical lamps of the preferred embodiments of this invention, are generally designated as L-1 (FIGS. 1-2), L-2 (FIG. 3), and L-3 (FIG. 5) and are designed to provide bright illumination in the area of surgery with a central portion of the light field being more brightly illuminated. It is understood that lamps L-1, L-2 and L-3 of the present invention may be used in applications other than surgery when good illumination is required.

Referring to FIGS. 1 and 2, the lamp L-1 includes lamp bowl-shaped housing 12 having a mounting means 14 on the upper portion thereof to operably mount lamp L-1 to a lamp support, generally designated by the letter S, of the various types currently known in the art and, further, having a concave reflector 16 disposed therein. The bowl-shaped or concave reflector 16 has a first closed upper end 16a and a second open bottom end 16b. The concave reflector 16, further has a reflective interior, concave surface 16c, which can be highly polished stainless steel or other mirrored finish for reflecting light rays into the general area where surgery is to be performed.

A central reflective means 18, preferably an inverted conical reflector, having upper base 18a and apex 18b, is mounted within concave reflector 16. In the preferred embodiment, the horizontal cross section of central reflective means 18 is circular. Base end 18a is mounted at closed end 16a of concave reflector 16 and apex 18b is positioned vertically downward toward open end 16b of the concave reflector 16. The conical reflector 18 has reflective exterior surface 18c which can be highly polished stainless steel or other mirrored finish for reflecting light rays downwardly through concave reflector open end 16b.

A circular, tubular light source 20, seen best in FIG. 2, preferably a circular fluorescent tube, is mounted within concave reflector 16 by light source mounting means 22. A fluorescent-type light source generates very little heat, but yet provides a light color temperature in the preferred range of about 4800 degrees kelvin. A greater amount of heat than that generated by the present invention tends to fatigue the surgical staff and accelerate the drying of tissue exposed during surgery. The light source mounting means 22 is a series of clips or brackets attached to the inner concave reflective surface 16c of reflector 16, which brackets encircle the light source 20. Light source 20 is mounted within concave reflector 16 concentrically about reflector 18, also centered about longitudinal axis 18d. Handle means 24 is detachably mounted to apex 18b of inverted conical reflector 18 and is used in cooperation with the support means S to position the light over the area to be illuminated. Handle means 24 may be removably attached to the apex 18b by and suitable connection so that handle means can be sterilized. In using handle means 24, the apex 18b may be truncated to provide a bottom flat surface on which to mount a connection means to connect the handle means 24 to the inverted conical reflector 18. It is understood, however, that the handle means could be located alternatively elsewhere on lamps L-1, L-2, or L-3.

One such way to provide for removable attachment of handle means 24 (FIG. 6) is to secure nut 24a within conical reflector 18 at the apex 18b thereof. Handle means 24 includes threaded stud 24b disposed in the end thereof. Handle means 24 may be removably attached by screwing threaded stud 24b into nut 24a.

Power supply means 26 is a transformer for providing a stable low voltage electrical supply to light source 20 by power cable 26a. Since power supply means 26 has a propensity to radiate heat, it may be mounted in the power line 26a remote from housing 12, allowing surgical lamp L to remain relatively cool. The removal of power supply means 26 from the lamp housing 12, further, tends to make surgical Lamp L-1 lighter and less cumbersome.

In the operation of Lamp L-1, referring to FIG. 2, circular tubular light source 20 (FIG. 1) illuminates a light field formed with incident light rays 20a and reflected light rays 20b from concave reflector 16. Reflected light rays 20c, are radially inwardly directed rays emitted by light source 20, which are reflected off of the reflective surface 18c of inverted conical reflector 18 and shine downwardly in a concentrated small circular area immediately below conical reflector 18 providing an area 21a of greater illumination in the central portion of the illuminated area 21. Further, the light rays 20d emitted upwardly and radially outwardly from light source 20 are reflected downwardly off a reflective concave surface 16c over the entire illuminated area 21.

Referring to FIG. 3 and embodiment L-2 for the lamp of this invention, a plurality of circular tubular light sources may be employed. In embodiment L-2, the housing 12 and inverted cone 18 are basically the same as in L-1, and so the same numbers and letters are used to designate substantially the same elements. In L-2, a first circular tubular light source 28, having outer diameter 28a, is mounted within concave reflector 16 and concentrically about inverted conical reflector 18 as described above. A second circular tubular light source 30, having the same outer diameter 30a as that of light source 28, is successively mounted therebelow, also concentrically about reflector 18, providing a greater amount of illumination to light field 21 and to area 21a of greater illumination. The inwardly directed light rays from light sources 28 and 30 reflect off of inverted cone 18 to provide the central area 21a of concentrated light. The outwardly directed light rays from the light sources 28 and 30 are reflected off of the interior reflective surface 16c to provide the light field 21.

Referring to FIG. 5 and embodiment L-3 for the lamp of this invention, yet another arrangement of a plurality of tubular light sources may be employed. The housing 12 and inverted cone 18 are, again, basically the same as in L-1 and L-2, and again, the same numbers and letters are used to designate substantially the same elements. In L-3, a first circular tubular light source 28, having an outer diameter 28a, is mounted within concave reflector 16 and concentrically about inverted conical reflector 18 as described above. A second circular tubular light source 30 having a greater outer diameter 30a, is mounted therebelow and, successively, a third circular tubular light source 32 having even a greater diameter 32a, is mounted immediately below second light source 30. These light sources 28, 30 and 32 are mounted adjacent to reflective surface 16c, wherein embodiments L-1 and L-2, the light sources such as 20 are mounted adjacent to conical reflector 18. As in embodiment L-2, embodiment L-3 provides a greater amount of illumination to light field 21 and area 21a of greater illumination than embodiment L-1. The inwardly directed rays from light sources 28, 30 and 32 reflect off of inverted cone 18 to provide the central area 21a of concentrated light. The outwardly directed light rays from the light sources 28, 30 and 32 are reflected off of the interior reflective surface 16c to provide the light field 21.

Figure 6:
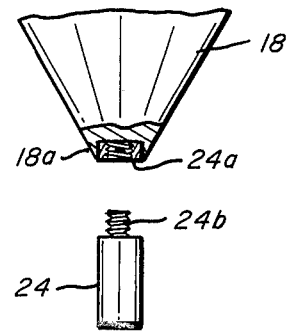
FIG. 6 is a view partly in section of the inverted conical reflector illustrating the handle means attachment means.

Surgical lamp L-1, L-2 or L-3 of the present invention may be "gang mounted" wherein a plurality of surgical lamps L-1, L-2 or L-3 are mounted with a lamp support S-1 as illustrated in FIG. 4, or it may be track mounted over an operating table as seen in FIGS. 5 and 6. Lamp support S-1, illustrated in the different forms in FIG. 4, is similar to type manufactured by the Castle Company of Rochester, New York, in their Castle Daystar Selectra Surgical Light System.

Figure 7:
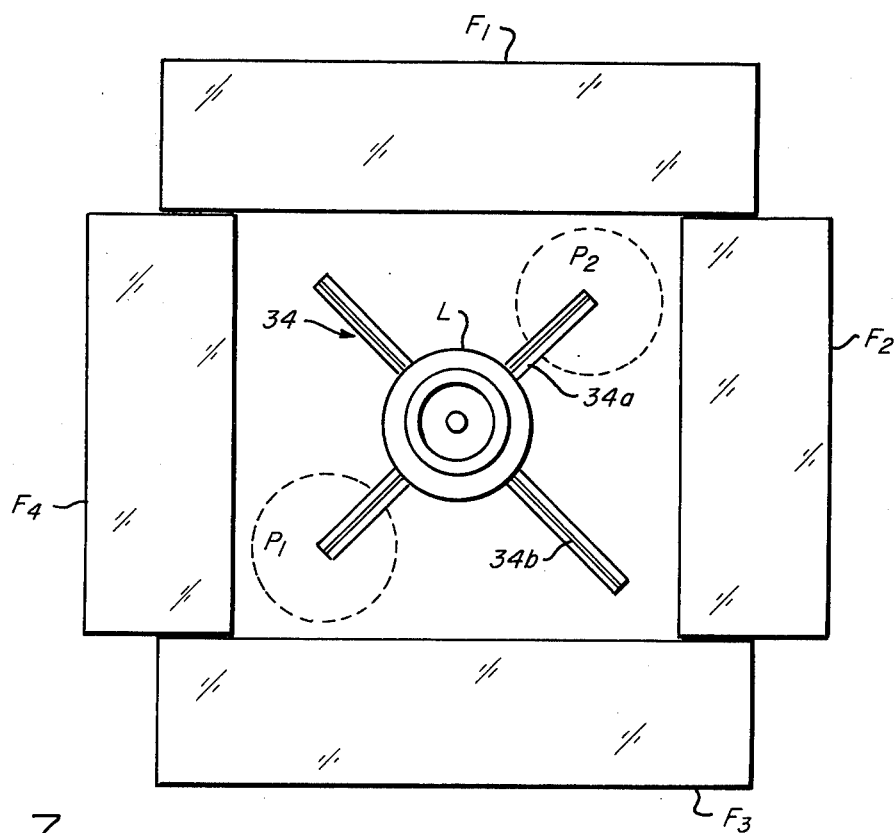
FIG. 7 is a plan view of the lamps of any of the three embodiments of the present invention mounted within a border of conventional fluorescent lamps overhead in an operating room.

The lighting system illustrated in FIG. 7 is comprised of conventional fluorescent-type lighting fixtures F-1, F-2, F-3 and F-4, mounted about track transport system 34. As seen in FIG. 7, surgical lamp L-1, L-2 or L-3 may be moved from position P-1 to P-2 along track 34a or in like manner along track 34b, in order to position light field 21 over the operating table and central light area 21a of greater illumination over the immediate area of surgery. Additionally, lamp L-1, L-2 or L-3 and track transport system 32 may be recessed in the ceiling.

The foregoing disclosure and description of the invention are illustrative and explanatory thereof, and various changes in size, shape and materials as well as in the details of the illustrated construction may be made without departing from the spirit of the invention.

I claim:
1. An improved operating room surgical lamp comprising:
    a lamp housing having a mounting means thereon adaptable to be mounted with a suitable support;
    said lamp housing having an interior concave reflective surface, said lamp housing having a first closed end and a second open end, said concave reflective surface positioned to reflect light out said second open end to illuminate a desired area;

a central reflective means mounted within said lamp housing at said closed end, said central reflective means having a reflective surface thereon to reflect light to a central position in the light field; and a tubular light source mounted within said lamp housing about said central reflective means for emitting light rays outwardly to reflect off of said interior concave reflective surface of said housing and for emitting light rays inwardly to reflect off of said central reflective means to illuminate a work area.

2. The structure set forth in claim 1 wherein:
said tubular light source is circular.

3. The structure set forth in claim 2 wherein:
said tubular light source is of a fluorescent-type.

4. The structure set forth in claim 1 wherein:
said central reflective means is circular in cross-section.

5. The structure set forth in claims 1 or 3 wherein:
said central reflective means is an inverted cone.

6. The structure set forth in claims 1 or 3 wherein: said central reflective means is a frusto-conical section.

7. The structure set forth in claim 3 wherein:
said tubular light source includes a plurality of fluorescent lights of equal overall diameter successively mounted.

8. The structure set forth in claim 3 wherein:
said tubular light source includes a first fluorescent light and a second fluorescent light of greater overall diameter mounted thereunder.

9. The structure set forth in claim 1, wherein the improved operating room surgical lamp further comprises:

a handle means operably mounted onto said central reflective means for positioning the light field over the area to be illuminated.

10. The structure set forth in claim 9 wherein:
said handle means is detachably mounted.

11. The structure set forth in claim 1, wherein:
said tubular light source, said central reflective means and said interior concave reflective surface cooperating to provide that light reflected off of said central reflective means forms a central spot of a higher intensity than light reflected off of said interior concave reflected surface.

* * * * *